(12) United States Patent
Roh et al.

(10) Patent No.: US 9,301,969 B2
(45) Date of Patent: Apr. 5, 2016

(54) TREATMENT OF NEURODEGENERATIVE DISEASES BY TARGETING MIRNA

(75) Inventors: Jae-Kyu Roh, Seoul (KR); Sang Kun Lee, Seoul (KR); Man Ho Kim, Seoul (KR); Kon Chu, Seoul (KR); Keun-Hwa Jung, Seoul (KR); Soon-Tae Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 23 days.

(21) Appl. No.: 13/822,641

(22) PCT Filed: Sep. 9, 2011

(86) PCT No.: PCT/KR2011/006718
§ 371 (c)(1),
(2), (4) Date: Mar. 13, 2013

(87) PCT Pub. No.: WO2012/036433
PCT Pub. Date: Mar. 22, 2012

(65) Prior Publication Data
US 2013/0184331 A1    Jul. 18, 2013

(30) Foreign Application Priority Data
Sep. 13, 2010 (KR) .................. 10-2010-0089651

(51) Int. Cl.
*A61K 31/7088* (2006.01)
*A61K 31/7105* (2006.01)
*A61K 31/711* (2006.01)
*C12Q 1/68* (2006.01)

(52) U.S. Cl.
CPC ............ *A61K 31/7088* (2013.01); *A61K 31/711* (2013.01); *A61K 31/7105* (2013.01); *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2005/0261218 A1* | 11/2005 | Esau et al. | 514/44 |
| 2006/0185027 A1* | 8/2006 | Bartel et al. | 800/14 |
| 2008/0279846 A1 | 11/2008 | Shi et al. | |
| 2008/0313773 A1 | 12/2008 | Chua et al. | |
| 2009/0246136 A1* | 10/2009 | Williams et al. | 424/9.1 |
| 2011/0257244 A1* | 10/2011 | Manoharan et al. | 514/44 A |

OTHER PUBLICATIONS

Chen, et al. (2010) microRNA-1 and microRNA-206 regulate skeletal muscle satellite cell proliferation and differentiation by repressing Pax7, Journal of Cell Biology, v.190(5):867-79.*
Zhang, et al. (2006) microRNAs exhibit high frequency genomicalterations in human cancer, PNAS, v.103(24):9136-41.*
International Search Report for PCT/KR2011/006718.

* cited by examiner

*Primary Examiner* — Jennifer McDonald
(74) *Attorney, Agent, or Firm* — Harness, Dickey & Pierce, P.L.C.

(57) ABSTRACT

The present invention relates to a pharmaceutical composition for preventing or treating neurodegenerative diseases by targeting a specific miRNA. In addition, the present invention relates to a kit for diagnosing neurodegenerative diseases. A miR-206 target found in the present invention, which is highly expressed in both animal models of Alzheimer's disease and human brain samples, is a substantial treatment target selected without artifact errors. An antisense oligonucleotide of the present invention as an inhibitor for miR-206 suggests a successful result in treatment of neurodegenerative diseases by targeting miRNA. The antisense oligonucleotide of the present invention inhibits the function of miR-206 to greatly increase the levels of BDNF and IGF-1 and to increase the regeneration of synapses, thereby treating neurodegenerative diseases, particularly Alzheimer's disease.

2 Claims, 18 Drawing Sheets

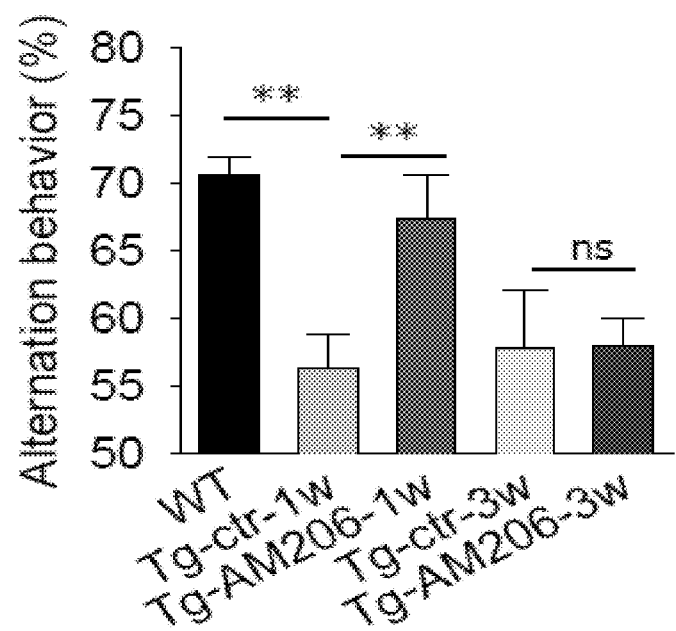

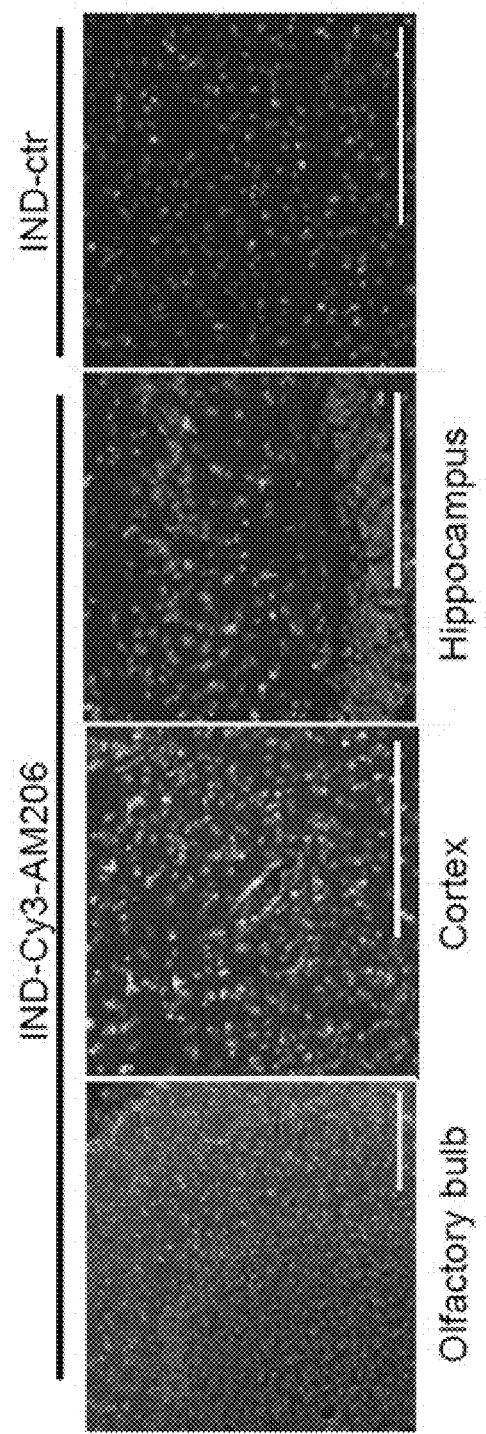

TREATMENT OF NEURODEGENERATIVE DISEASES BY TARGETING MIRNA

CROSS REFERENCE TO RELATED APPLICATIONS AND CLAIM OF PRIORITY

This patent application is a National Phase application under 35 U.S.C. §371 of International Application No. PCT/KR2011/006718, filed on Sep. 9, 2011, entitled TREATMENT OF NEURODEGENERATIVE DISEASES BY TARGETING MIRNA, which claims priority to Korean Patent Application No. 10-2010-0089651, filed on Sep. 13, 2010, entire contents of which are incorporated herein by reference.

FIELD OF THE INVENTION

The present invention relates to a pharmaceutical composition for preventing or treating a neurodegenerative disease by targeting a specific miRNA. In addition, the present invention relates to a kit for diagnosing a neurodegenerative disease.

DESCRIPTION OF THE RELATED ART

Alzheimer disease (AD) is the most common form of dementia in the elderly characterized by progressive cognitive decline, neuronal degeneration, and the accumulation of extracellular deposits of amyloid (senile plaques) and intracellular inclusions (neurofibrillary tangles; NFT) (Braak and Braak, 1996; Querfurth, 2010). Currently, no proven disease-modifying treatment is available for AD. The major molecular mechanism of AD includes misfolded proteins, oxidative and inflammatory damages, and energy failure, which finally leads to synaptic dysfunction (Querfurth et al., 2010). Synapses are the initial target of AD pathogenesis and the changes of synaptophysin has been correlated with cognitive declines (Selkoe, Science, 2002). AD brains have low levels of brain-derived neurotrophic factor (BDNF), which is a master regulator of synaptic plasticity, synaptogenesis, and neurogenesis (Phillips et al., 1991; Bramham et al., 2005; Ernfors, Trends Neurosci, 2003). Thus, the modulation of BDNF has been suggested for AD (Nagahara, Nat med, 2009), although any safe and effective method has not been developed.

MicroRNAs (miRNA) are 21- to 23-nucleotide small RNA molecules that regulate gene expression by degradation or translational repression of target mRNAs (Kim et al., 2009). The miRNAs are involved in a variety of physiological phenomena and diseases (Kim et al., 2009). In central nervous system, the loss of Dicer, a key regulator of miRNA biogenesis, induces neurodegeneration, suggesting that balanced miRNAs expression plays an important role in nervous system (Schaefer et al, 2007; Cueller et al., 2008). Several miRNAs, such as miR-8, 9/9*, and 133b, involved in neurodegeneration have been discovered (Karres et al., 2007; Kim, Science, 2007; Packer, J Neurosci, 2008). In AD researches, several changes in the microRNA expressions and their implication in AD pathogenesis have been reported as well (Maes et al., 2009; Hebert, Trends, 2009). Although these studies expanded the understanding of the pathogenesis of AD, any direct therapeutic application of miRNAs in AD has not been tried so far.

Throughout this application, several patents and publications are referenced and citations are provided in parentheses. The disclosure of these patents and publications is incorporated into this application in order to more fully describe this invention and the state of the art to which this invention pertains.

SUMMARY

The present inventors have made intensive studies to discover target molecules for treating a neurodegenerative disease, particularly Alzheimer disease, and to develop drug which targets the molecules. As a result, the present inventors have found out that miR-206 is highly expressed in a neurodegenerative disease, and an antisense oligonucleotide which targets miR-206 regenerates synapses and recovers memory, thereby a neurodegenerative disease may be treated.

It is an object of the present invention to provide a pharmaceutical composition for preventing or treating a neurodegenerative disease.

It is another object of the present invention to provide a kit for diagnosing a neurodegenerative disease.

Other objects and advantages of the present invention will become apparent from the detailed description to follow taken in conjugation with the appended claims and drawings.

In one aspect of the present invention, there is provided a pharmaceutical composition for preventing or treating a neurodegenerative disease, comprising:

(a) a pharmaceutically effective amount of an antisense oligonucleotide having a complementary sequence to a nucleotide sequence spanning the position 2 to the position 7 of the nucleotide sequence as set forth in SEQ ID NO:1; and (b) a pharmaceutically acceptable carrier.

In another aspect of the present invention, there is provided a method for preventing or treating a neurodegenerative disease, comprising administering to a subject in need thereof a pharmaceutical composition comprising:

(a) a pharmaceutically effective amount of an antisense oligonucleotide having a complementary sequence to a nucleotide sequence spanning the position 2 to the position 7 of the nucleotide sequence as set forth in SEQ ID NO:1; and (b) a pharmaceutically acceptable carrier.

The present inventors have made intensive studies to discover target molecules for treating a neurodegenerative disease, particularly Alzheimer disease, and to develop drug which targets the molecules. As a result, the present inventors have found out that miR-206 is highly expressed in a neurodegenerative disease, and an antisense oligonucleotide which targets miR-206 regenerates synapses and recovers memory, thereby a neurodegenerative disease may be treated.

The term used herein "antisense oligonucleotide" encompasses nucleic acids-based molecules complementary to a target miRNA, particularly a seed sequence of the target miRNA to form duplex with the target miRNA. Therefore, the term used herein "antisense oligonucleotide" may be also described as "a complementary nucleic acid-based inhibitor".

The nucleotide sequence as set forth in SEQ ID NO:1 represents a mature sequence of miR-206. A nucleotide sequence spanning the position 2 to the position 7 of the nucleotide sequence as set forth in SEQ ID NO:1 is a seed sequence of miR-206. Typically, a seed sequence of miRNA is a very important sequence to recognize target and it is conserved in various species (Krenz, M. et al., J. Am. Coll Cardiol 44:2390-2397 (2004); H. Kiriazis, et al, Annu. Rev. Physiol. 62:321 (2000)). Therefore, the present antisense oligonucleotide has a complementary sequence to a nucleotide sequence spanning the position 2 to the position 7 of the nucleotide sequence as set forth in SEQ ID NO:1 as the seed sequence of miRNA-206, and it may suppress miR-206.

The term used herein "complementary" in conjunction with an antisense oligonucleotide means that the antisense oligonucleotide is sufficiently complementary to hybridize selectively to miR-206 target under the designated hybridization or annealing conditions, preferably physiological conditions, encompassing the terms "substantially complementary" and "perfectly complementary", preferably perfectly complementary.

According to a preferable embodiment, the antisense oligonucleotide used as an active ingredient in the present invention has a complementary sequence to a nucleotide sequence spanning the position 1 to the position 8, the position 2 to the position 8 or the position 2 to the position 7 of the nucleotide sequence as set forth in SEQ ID NO:1 (i.e., a mature sequence of miR-206). Most preferably, the antisense oligonucleotide used as an active ingredient in the present invention has a complementary sequence to the entire sequence of the nucleotide sequence as set forth in SEQ ID NO:1 (i.e., a mature sequence of miR-206).

In the present invention, the antisense oligonucleotide includes various molecules. The antisense oligonucleotide is DNA or RNA molecule, more preferably RNA molecule. Alternatively, the antisense oligonucleotide used in the present invention is ribonucleotide (RNA), deoxyribonucleotide (DNA), 2'-O-modified oligonucleotide, phosphorothioate-backbone deoxyribonucleotide, PNA (peptide nucleic acid) or LNA (locked nucleic acid). Preferably, 2'-O-modified oligonucleotide is 2'-O-alkyl oligonucleotide, more preferably 2'-O—$C_{1-3}$ alkyl oligonucleotide, and most preferably 2'-O—$C_{1-3}$ methyl oligonucleotide.

As mentioned above, the present antisense oligonucleotide encompass to a nucleic acid-based inhibitor having a complementary sequence to miRNA. The present antisense oligonucleotide includes, for example, an antisense oligonucleotide in a narrow sense, an antagomir and an inhibitory RNA molecule.

The term "antagomir" is a single-strand chemically-modified ribonucleotide, and it has at least a partially complementary sequence to miR-206, preferably a perfectly complementary sequence to miR-206. The antagomir includes one or more modified oligonucleotide (e.g., 2'-O-methyl-sugar modification). According to an embodiment, the antagomir includes only a modified oligonucleotide. The antagomir includes one or more phosphorothioate bond, whereby it has partial or perfect phosphorothioate backbone. In order to improve in vivo delivery and stability, the antagomir may combine cholesterol or other region at its 3'-end. To inhibit miR-206, a suitable length of the antagomir is 7-50 nucleotides, preferably 10-40 nucleotides, more preferably 15-30 nucleotides, and most preferably 20-25 nucleotides.

Functional inhibitory of miR-206 may be achieved by administering a conventional antisense oligonucleotide. The antisense oligonucleotide is ribonucleotide or deoxyribonucleotide. Preferably, the antisense oligonucleotide includes at least one chemical modification. The antisense oligonucleotide may include one or more LNA (locked nucleic acid). LNA is a modified ribonucleotide with a "locked form" in which an extra bridge is included between 2' to 4' carbon on ribose, whereby an oligonucleotide having LNA has improved thermal-stability.

Alternatively, the antisense oligonucleotide may include PNAs (peptide nucleic acids), which include peptide-based backbone instead of sugar-phosphate backbone. The antisense oligonucleotide may include other chemical modifications, for example, sugar modifications such as 2'-O-alkyl (e.g., 2'-O-methyl and 2'-O-methoxyethyl), 2'-fluoro and 4'-thio modification; and backbone modification such as phosphorothiate, morpholinos or phosphonocarboxy linkage (e.g., U.S. Pat. No. 6,693,187 and No. 7,067,641).

In an embodiment, a suitable antisense oligonucleotide is 2'-O-methoxyethyl "gapmer" which includes 2'-O-methoxyethyl-modified ribonucleotide at 5'-end and 3'-end and has at least 10 deoxyribonucleotides in the middle. The "gapmer" can trigger RNase I-dependent degradation mechanism of RNA target. The antisense oligonucleotide length is 7-50 nucleotides, preferably 10-40 nucleotides, more preferably 15-30 nucleotides, and most preferably 20-25 nucleotides.

Another approach to inhibit function of miR-206 is administering inhibitory RNA molecules and the inhibitory RNA molecules include a complementary sequence to a mature sequence of miR-206. These inhibitory RNA molecules include siRNA (small interfering RNA), shRNA (short hairpin RNA) and ribozyme.

A disease which may be treated by the present pharmaceutical composition includes various neurodegenerative diseases, preferably Alzheimer's disease, dementia, Huntington's disease, Parkinson's disease or amyotrophic lateral sclerosis, most preferably Alzheimer's disease.

As shown in the following Examples, the present antisense oligonucleotide inhibits the function of miR-206 to greatly increase the levels of BDNF and IGF-1 and to increase the regeneration of synapses, thereby treating a neurodegenerative disease, particularly Alzheimer's disease.

The pharmaceutically acceptable carrier included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable excipients and formulations are described in detail in *Remington's Pharmaceutical Sciences* (19th ed., 1995).

The pharmaceutical composition of the present disclosure may be administered orally or parenterally. When the composition of the present disclosure is administered parenterally, the pharmaceutical composition of the present disclosure may administer with intravenous injection, nasal injection, local injection, intraventricular injection, spinal injection, subcutaneous injection, intraperitoneal injection and transdermal injection.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. According to a preferable embodiment, the pharmaceutical composition of the present invention may be administered with a daily dose of 0.001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. The formulation may be in the form of a solution in oily or aqueous medium, a suspension, a syrup, a emulsion, an extract, an elixir, a powder, a granule, a tablet or a capsule, and may further include a dispersant or stabilizer.

The successful results are first proposed by the present antisense oligonucleotide as inhibitor to miR-206 in treatments of a neurodegenerative disease targeting miRNA.

In still another aspect of the present invention, there is provided a kit for diagnosing a neurodegenerative disease, comprising a nucleotide sequence of miRNA selected from the group consisting of miR-424*, miR-18b*, miR-135a*, miR-1228, miR-320, miR-296-5p, miR-557, miR-338-5p, miR-206, miR-92a, miR-1238, miR-513a-5p, miR-423-5p, miR-188-5p, miR-140-3p, miR-575, miR-640, miR-1237, miR-191* or miR-134; or its complementary sequence or fragment.

In further aspect of the present invention, there is provided a method for detecting a marker for a neurodegenerative disease, comprising detecting the expression of miR-424*, miR-18b*, miR-135a*, miR-1228, miR-320, miR-296-5p, miR-557, miR-338-5p, miR-206, miR-92a, miR-1238, miR-513a-5p, miR-423-5p, miR-188-5p, miR-140-3p, miR-575, miR-640, miR-1237, miR-191* or miR-134 in human biological samples, whereby information for diagnosing or predicting a neurodegenerative disease is provided.

The nucleotide sequences of the miR-206 molecules are determined in GenGank.

Most preferably, the miRNA molecule is miR-206.

The present kit for diagnosing may be used for various neurodegenerative diseases, preferably Alzheimer's disease, dementia, Huntington's disease, Parkinson's disease or amyotrophic lateral sclerosis, and most preferably Alzheimer's disease.

The present kit may further include, in addition to the above-described components, other components. For instance, where the present kit is applied to PCR amplification, the kit may optionally include the reagents required for performing PCR amplification such as buffers, DNA polymerase (e.g., thermostable DNA polymerase obtained from Thermus aquaticus (Taq), Thermus thermophilus (Tth), Thermus filiformis, Thermis flavus, Thermococcus literalis or Pyrococcus furiosus (Pfu)), DNA polymerase cofactors, and dNTPs. The present kit is adopted to contain the constituents afore-described in separate packaging or compartments.

According to a preferable embodiment, the present kit may be a microarray. According to a preferable embodiment, the present kit is a gene amplification kit.

Where the present kit is a microarray, a probe is immobilized on the solid surface. Where the present kit is a gene amplification kit, the kit includes a primer.

The probe or the primer used in the present kit for diagnosing has a complementary sequence to PRDX 1 nucleotide sequence. The term "complementary" is used herein to mean that primers or probes are sufficiently complementary to hybridize selectively to the above-described nucleotide sequence under some specific hybridization or annealing conditions. Therefore, the term "complementary" has a different meaning to the term "perfectly complementary", and the present primer or the probe may include one or more mismatch base sequences to the extent that the probe or the primer may be selectively hybridized with the above-described nucleotide sequence.

Where the primer or the probe is prepared, the nucleotide sequence of the present miRNA is determined in Genbank and the primer or the probe may be designed with referring to descriptions indicated hereinabove.

The miRNA expression level of a sample from a subject is analyzed by the present kit or method, for example, RT (reverse transcriptase)-PCR or real-time-PCR method (see Sambrook, J. et al., Molecular Cloning. A Laboratory Manual, 3rd ed. Cold Spring Harbor Press (2001)). Where the expression level shows at least 1.5-fold (preferably at least 2-fold, and most preferably at least 3-fold) higher than a normal control group, the subject may be determined to have or to be in a high risk of a neurodegenerative disease, particularly, Alzheimer's disease.

The features and advantages of the present invention will be summarized as follows:

(a) The present invention provides miR-206 as target for treating a neurodegenerative disease, particularly, Alzheimer's disease.

(b) A miR-206 target found in the present invention, which is highly expressed in both animal models of Alzheimer's disease and human brain samples, is a substantial treatment target selected without artifact errors.

(c) An antisense oligonucleotide of the present invention as an inhibitor for miR-206 suggests a successful result in treatment of a neurodegenerative disease by targeting miRNA.

(d) The antisense oligonucleotide of the present invention inhibits the function of miR-206 to greatly increase the levels of BDNF and IGF-1 and to increase the regeneration of synapses, thereby treating a neurodegenerative disease, particularly Alzheimer's disease.

DETAILED DESCRIPTION

Figure 1A:
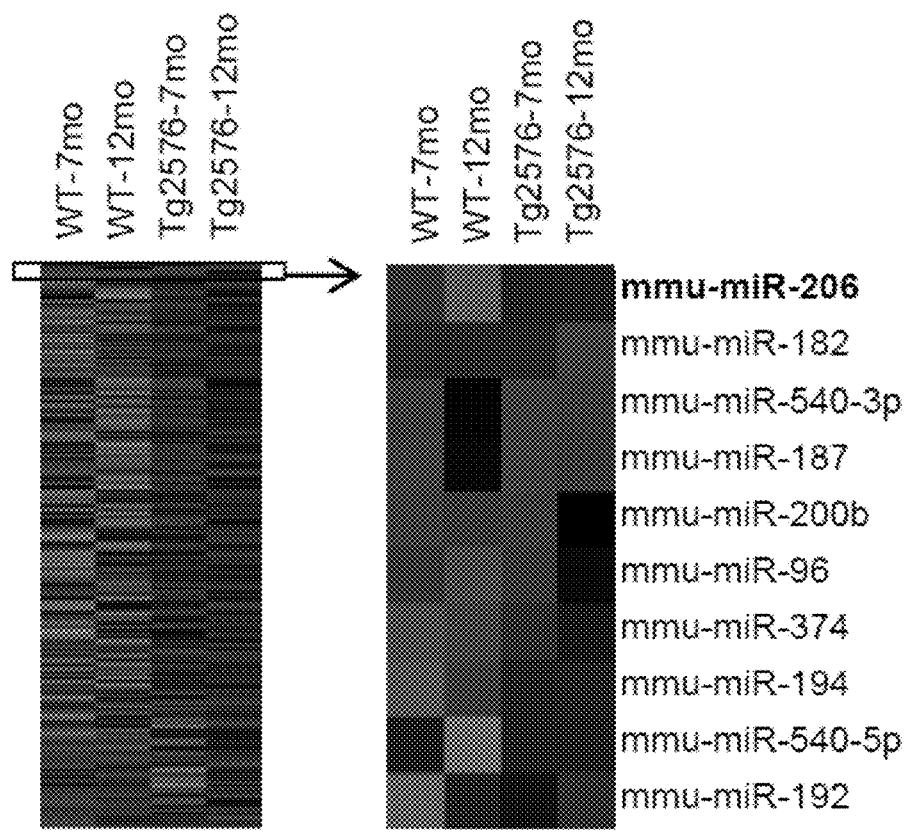
FIG. 1 represents miR-206 of upregulation in brain of Alzheimer's disease. (a) Microarray analysis of 7- and 12-month-old WT and Tg2576 mice revealed differentially regulated miRNAs. Red indicates higher expression (higher Z-score) than green. The miRNAs are listed in order (from top to bottom) according to the relative mean expression (Tg2576/WT). The heat map at right shows a magnification of the image indicated by the rectangle on the left (Mmu, *Mus musculus*). (b) Real-time PCR (graph) and RT-PCR (gel) confirmed that miR-206 levels are higher (n=4 per group) in 12-month-old Tg2576 mice than in 12-month-old WT mice. sno202 RNA was used as an internal control. (c) In situ hybridization for miR-206 indicated enhanced expression of miR-206 in 12-month-old Tg2576 mice (Scale bar, 25 μm). (d) Real-time PCR showed that addition of Aβ42 peptides to cell cultures significantly increased the level of miR-206 in Neuro-2a cells but not in HUVEC. (e) In human temporal cortex, real-time PCR showed up-regulation of miR-206 in AD brains compared to the control brain (n=4 per group). *$P<0.05$, and **$P<0.01$. Bars indicate mean±s.e.m.

The present invention will now be described in further detail by examples. It would be obvious to those skilled in the art that these examples are intended to be more concretely illustrative and the scope of the present invention as set forth in the appended claims is not limited to or by the examples.

EXAMPLE

Material and Methods
AD(Alzheimer's Disease) Model

This study was approved by Institutional Animal Care and Use Committee of Seoul National University Hospital, which was accredited by the Association for the Assessment and Accreditation of Laboratory Animal Care International. Tg2576 mice (Taconic, Hudson, N.Y., USA), which express the human 695-amino acid isoform of amyloid precursor protein containing the Swedish double mutation (Swedish mutation; Lys670→Asn, Met671→Leu) under the control of the prion promoter (Hsiao et al., 1996), were used as a transgenic model of AD. The transgenic and wild type mice were maintained in separate cages at room temperature (25° C.) with free access to food and water under a 12-hour light-dark cycle, and used for miRNA analysis at 7 month or 12 months of age.

miRNA Microarray

Agilent miRNA Microarray 8×15K kits for mouse or human (Agilent, Santa Clara, Calif.) were used. RNA from mice brains were pooled (two mice per pool). Frozen samples of human temporal cortex were obtained from the Brain Bank of Boston University Alzheimer's Disease Center (Boston, Mass.). The present inventors used mouse samples satisfying the following RNA quality criteria: 260/280 ratio >1.8, 260/230 ratio >2.0, 28S/18S rRNA ratio >1.6, and RNA integrity number >8.0. Because human autopsy samples undergo post-mortem degradation of RNA, AD and control samples were matched for the post-mortem intervals.

Real-Time PCR

Real-time PCR for miRNA was performed using a mir-Vana qRT-PCR miRNA Detection Kit and primer sets (Applied Biosystems, Foster City, Calif.). The snoRNA202 level, measured using an endogenous snoRNA202 detection kit (Ambion-Applied Biosystems), was used to normalize miRNA levels. The miRNAs were amplified for 35 cycles and visualized following electrophoresis on a 1.0% agarose gel. Real-time PCR for BDNF mRNA expression was performed using primers and probe from TaqMan gene expression assay (Applied Biosystems).

In situ Hybridization for miRNA

The present inventors detected miRNA in situ expression by the use of locked nucleic acids (LNAs), which are bi-cyclic RNA analogs that allow a significant increase in the hybridization temperature and thereby an enhanced stringency for short probes as required for miRNA detection (Obernosterer et al., 2007). The LNA probe for miRNA detection was purchased from Exiqon, and labeled to the frozen-sectioned tissue using a DIG 30 end labeling kit (Roche), as described (Obernosterer et al., 2007).

Targeted Gene Prediction of miRNAs

The miRNA mature sequence database was obtained from miRBase (http://www.mirbase.org). To find potential miRNA target sites in the mouse gene 3'-untranslated region (UTR), The present inventors used three different target prediction programs: TargetScan (http://www.targetscan.org), (Lewis, 2005) PicTar (http://pictar.mdc-berlin.de/), (Krek, 2005) and microT (http://diana.cslab.ece.ntua.gr/microT/) (Kiriakidou, 2004).

Treatment of Antagomir in AD Mice

Mice were anesthetized by intraperitoneal injection of 1% ketamine (30 mg/kg) and xylazine hydrochloride (4 mg/kg) and then positioned in a stereotaxic apparatus. Using a 30-guage Hamilton syringe, 1 μL of phosphate-buffered saline containing 0.5 nmol of the antagomir AM206 (2'-O-methylated-5'-cca cac acu ucc uua cau ucc a-3') or a scrambled sequence control antagomir (2'-O-methylated-5'-aag gca agc uga ccc uga agu u-3') (Bioneer, Daejon, South Korea) was injected over 5 min into the third ventricle at the following coordinates: antero-posterior, −1.06 mm; medio-lateral, 0.00 mm; dorso-ventral, −2 4 mm from the bregma. The needle was left in position for another 5 min and then gently removed. To visualize the distribution of AM206, mice were injected with Cy3-labeled AM206 (Cy3-2'-O-methylated-5'-cca cac acu ucc uua cau ucc a-3', Bioneer) instead of AM206. For intranasal administration of AM206, anesthetized mice were placed in a supine position with the head in an upright position. AM206 (or Cy3-labeled AM206; 5 nmol in 24 μL of 0.1% v/v diethylpyrocarbonate-treated distilled water) was administered by pipette in 4-μL drops (total 6 fractions), alternating between each nostril every 2 min. Control Tg2576 mice were age-matched and received an equal volume of vehicle.

Contextual and Cued Fear Conditioning

Fear conditioning was carried out as described previously (Jeon et al., 2008) in a fear-conditioning shock chamber system (Coulbourn Instruments, Whitehall, Pa., USA). For conditioning, mice were placed in the fear-conditioning apparatus chamber for 5 min and then given a 28-s acoustic conditioned stimulus, followed by a 0.7-mA shock applied to the floor grid for 2 s as an unconditioned stimulus. This was repeated three times with 60 s between each cycle. To assess contextual memory, 24 h after the conditioning the animals were placed back in the training apparatus without acoustic stimuli, and freezing behavior was observed for 5 min. To assess cued memory, the animals were placed in a chamber with different odor, floor, and visual cues 24 h after the conditioning, and their behaviors were monitored for 5 min. During the last 3 min of this test, animals were exposed to the acoustic stimulus. The fear response was quantified by measuring the length of freezing behaviors, defined as a crouching position with a lack of movement except for respiratory movements (Jeon et al., 2008).

Y Maze Test

Y-maze test was performed as previously described (Sarter et al., 1988). The maze was made of black-painted plastics and each arm was 35 cm long, 15 cm high, 5 cm wide and positioned at equal angles. Mice were placed at the end of one arm and allowed to move freely through the maze for 5 minutes. The series of arm entries was recorded visually and arm entry was considered to be completed when the hind paws of the mouse were completely placed in the arm. Alternation was defined as successive entries into the three arms on overlapping triplet sets. The % alternation was calculated as the ratio of actual to possible.

Western Blotting

Anesthetized mice were sacrificed by decapitation, and brains were immediately removed. Homogenates of each brain were serially processed for Western blotting as described previously (Lee et al., 2009), using antibodies against brain-derived neurotrophic factor (BDNF, Abcam), insulin-like growth factor-1 (IGF-1, Abcam), Notch3 (Abcam), MEOX2 (Abcam) or β-actin (Santa Cruz Biotechnology). Blots were developed by enhanced chemiluminescence reagents (Pierce, Rockford, Ill., USA) and digitally scanned (GS-700; Bio-Rad, Hercules, Calif., USA). The relative optical densities of each band relative to measured values of β-actin bands were determined using Molecular Analyst™ software (Bio-Rad). The levels of Aβ40 and Aβ42 in the homogenates brains were measured by Aβ Ultrasensitive ELISA kit (Invitrogen) according to the manufacturer's protocol.

Histologic Analysis of Tg2576 Mice

Animals were deeply anesthetized and perfused through the heart with 10 mL of cold saline and 10 mL of 4% paraformaldehyde in 0.1 M phosphate-buffered saline. Sections (20-μm thickness) were stained with 4',6-diamidino-2-phenylindole, *Ulex europaeus* I lectin (Vector Laboratories, Burlingame, Calif.) or antibodies against MAP2 (Chemicon-Millipore, Billerica, Mass.), GFAP (Santa Cruz Biotechnology, Santa Cruz, Calif.), synaptophysin or doublecortin (Abcam, Cambridge, Mass.). Optical densities from synaptophysin staining of the hippocampus were analyzed in three sequential coronal tissue sections from each mouse (500-μm interval, approximately −1.5 to −2 5 mm antero-posterior from the bregma) using Image-J (National Institutes of Health, Bethesda, Md.). Values are relative to those of control Tg2576 mice. In the neighboring three hippocampal sections (500-μm interval), the number of doublecortin-immunoreactive cells in the subgranular layer of the dentate gyrus was counted and normalized by the length of the dentate gyrus (1200 μm).

Dual Luciferase Assay

Oligonucleotides for the 3'-UTR positions of possible target genes were designed to contain SacI and XbaI restriction sites at the 5'- and 3'-ends, respectively, and were subcloned into the pmirGLO Dual-Luciferase miRNA target expression vector (Promega, Madison, Wis.). The transfection-ready luciferase reporter construct was used for the total 3'-UTR sequences of BDNF (SwitchDB, Menlo Park, Calif.). HeLa cells ($5 \times 10^4$ cells per well) were added to 24-well plates. After 24 hrs, cells were transfected with 30 pmol of miRNA-206 duplexes (or scrambled miRNA duplexes; Bioneer, Daejon, South Korea) and 50 ng of luciferase expression vectors using Lipofectamine 2000 (Invitrogen, Carlsbad, Calif.). Firefly and Renilla luciferase activities were assessed after 48 hrs using the Dual-Luciferase Reporter 1000 Assay System (Promega), and the normalized values (firefly luciferase activity/Renilla luciferase activity) were used for analysis.

Analysis of Dendritic Spine Density

Primary hippocampal neurons were cultured from embryonic E17 C57BL/6 mouse embryos. The neurons were cultured on polylysine-coated coverslips, which were suspended above an astrocyte feeder layer and maintained in N2 medium (Invitrogen). To generate Aβ oligomer, 5 mM Aβ42 peptide or scrambled Aβ peptide (Millipore) in dimethylsulfoxide was diluted to 100 μM with ice-cold culture medium, sonicated for 10 min, and incubated for 24 h at 4° C. At 3 weeks in culture, the neurons were treated with 5 μM Aβ oligomer. Concomitantly, 500 nM AM206 or scrambled antagomir were added to the culture medium. After 48 hrs, the neurons were fixed with 4% paraformaldehyde for 40 min, and stained with Phalloidin labeled with rhodamine (Invitrogen). The dendritic spines were observed with a LSM510 Meta Confocal microscope (Carl Zeiss). The spines were counted in randomly selected 100 dendritic segments from 30 cells in each group. Density was calculated for dendritic lengths of 10 μm.

Data Analysis and Statistics

Heat maps for miRNA expression were generated using the Z-score. The Mann-Whitney U test was used for inter-group comparisons between two groups, and the Kruskall-Wallis analysis of variance for comparisons between three or more groups. The Mann-Whitney U test was used for post-hoc inter-group comparisons. All statistical analyses were made using SPSS, version 17.0 (SPSS Inc., Somers, N.Y.). A two-tailed p-value below 0.05 was considered to indicate statistical significance.

Results
miRNA Signature of AD Transgenic Mice.

Figure 1B:
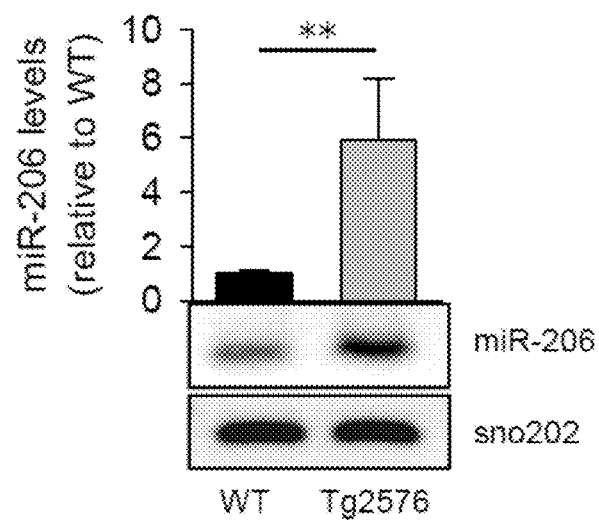

Based on the hypothesis that responsible miRNAs for the regulation of BDNF would be among the altered miRNAs in AD models, the present inventors first compared miRNA levels between 7- and 12-month old wild-type (WT) and Tg2576 mice, a transgenic model of AD, by using microarray (FIG. 1a). the present inventors chose these ages because Tg2576 mice show increased Aβ42 expression at 7 months and impaired memory at 12 months. The miRNA most up-regulated in both 7- and 12-month old Tg2576 mice was miR-206. Real-time PCR confirmed the up-regulation of miR-206 in 12-month old Tg2676 mice (FIG. 1b).

Figure 1C:
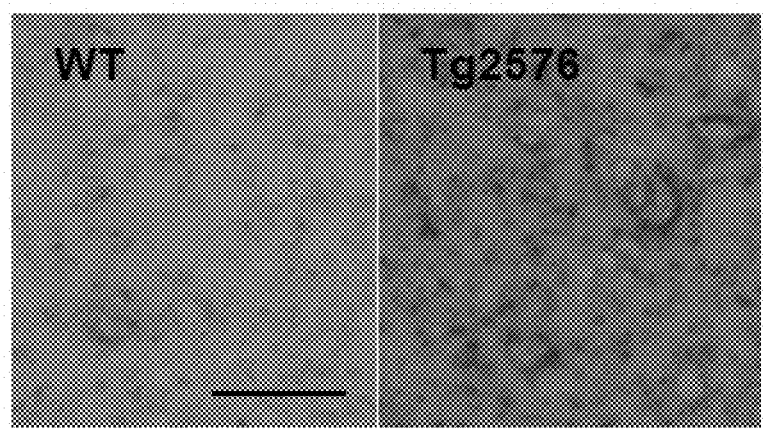
Figure 1D:
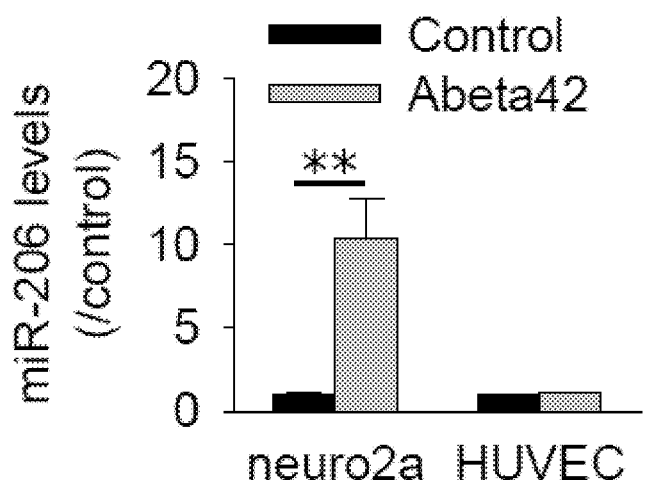
Figure 1E:
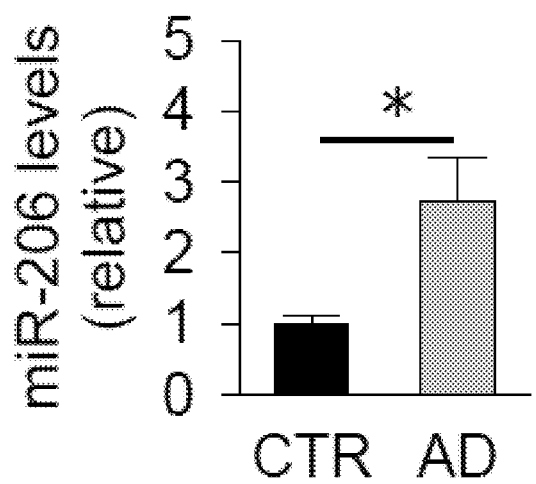

In situ hybridization also revealed enhanced and diffuse expression of miR-206 in the brains of 12-month old Tg2576 mice (FIG. 1c). Similarly, real-time PCR showed that Aβ42 increases the levels of miR-206 in Neuro-2a mouse neuroblastoma cells but not in human umbilical vein endothelial cells (HUVEC) (FIG. 1d). To determine whether these findings may also be relevant in human AD, the present inventors measured the level of miR-206 in human superior temporal cortex samples from four AD patients (Braak stage V, clinical dementia rating [CDR]3) and from four non-AD control subjects of similar age and sex (Braak stage I, CDR 0). In our brain bank, a post-mortem interval of approximately 3 to 3.5 hrs was the shortest practical time to obtain human brain tissues at autopsy. Because human autopsy samples undergo post-mortem degradation of RNA, and the 28S/18S rRNA ratio and RNA integrity number decreased after 2 hrs post-mortem when tested in mouse brains, AD and control samples were matched according to the post-mortem intervals. In this condition, real-time PCR confirmed that miR-206 was up-regulated in the AD brains compared to the control brains (FIG. 1e).

Therapeutic Application of Antagomir-206 in AD Model.

Figure 2A:
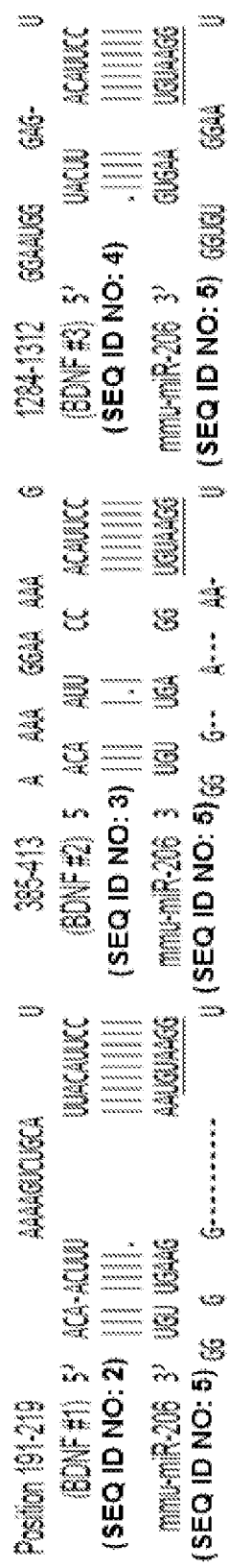
FIG. 2 represents modulation of BDNF by miR-206. (a) Three positions of the BDNF 3'-UTR (BDNF #1, #2, and #3) were predicted to be targets of miR-206. The seed sequence of miR-206 is underlined. (b) In luciferase assays using HeLa cells, transfection of miR-206 reduced the luciferase activities of vectors bearing BDNF #3 and total 3'-UTR of BDNF (tBDNF) (n=6 replicates). (c) In Neuro-2a cells and HUVEC, transfection with miR-206 reduced the level of BDNF protein as shown by Western blotting (left) and densitometry (right). The reduction was neutralized by co-transfection with AM206. Scr, scrambled sequence. (d) In Neuro-2a cells, Aβ oligomer treatment increased the level of miR-206 without significantly reducing BDNF mRNA (n=6 per group). (e) Aβ oligomer reduced BDNF protein levels in the cells and transfection with AM206 restored the BDNF protein level (Scr, scrambled sequence). (f) In mouse primary hippocampal neurons, Aβ oligomer reduced the dendritic spine density, which was prevented by AM206 treatment (Scale bar, 10 μm). (g) 12-month-old Tg2576 mice were injected in the third ventricle with Cy3-labeled AM206. At 24 h, fluorescence for Cy3-AM206 was distributed throughout the hippocampus and surrounding tissues (Scale bar, 100 μm). (h) Cy3-AM206 was taken up by MAP2-positive neurons, Ulex-lectin-positive endothelial cells, and GFAP-positive glial cells (Scale bar, 20 μm). (i) Western blotting (left) and densitometry (right) showed that intraventricular injection of Tg2576 mice with AM206 (Tg2576-AM206) significantly increased the whole brain level of BDNF compared to control (Tg2576-control) at 1 week after the injection (n=4 per group). *P<0.05, and **P<0.01. ns, not significant. Bars show mean±s.e.m.

Given the consistent upregulation of miR-206 in AD models, the present inventors then searched its target genes. Indeed, TargetScan, PicTar, and microT found three putative targets of miRNA-206 in the 3'-untranslated regions (UTRs) of the mice and human genes encoding BDNF (FIG. 2a). In support of this, the present inventors found that the level of miR-206 increases and the protein levels of BDNF decrease as Tg2576 mice age.

Figure 2B:
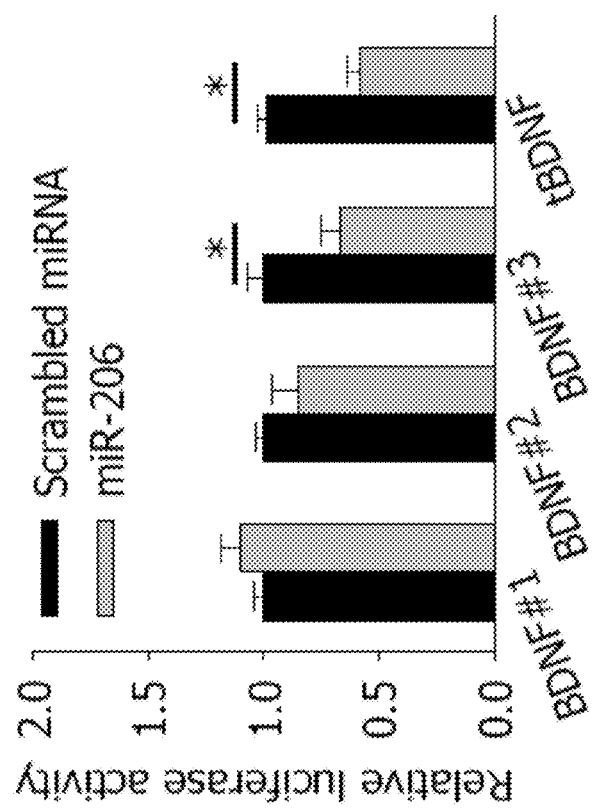
Figure 2C:
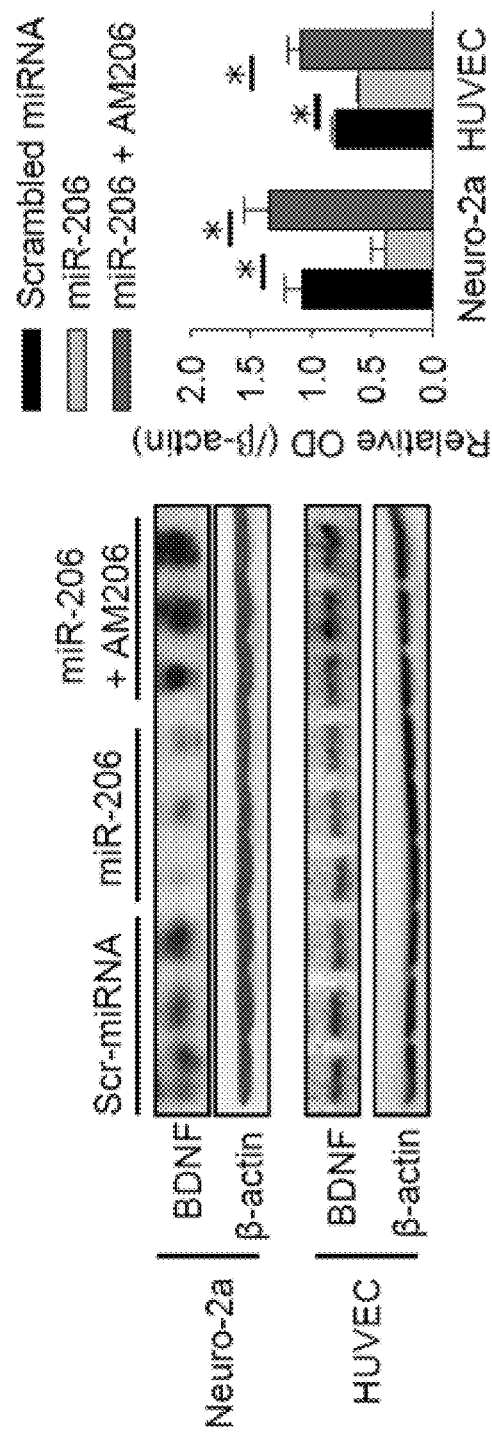
Figure 2D:
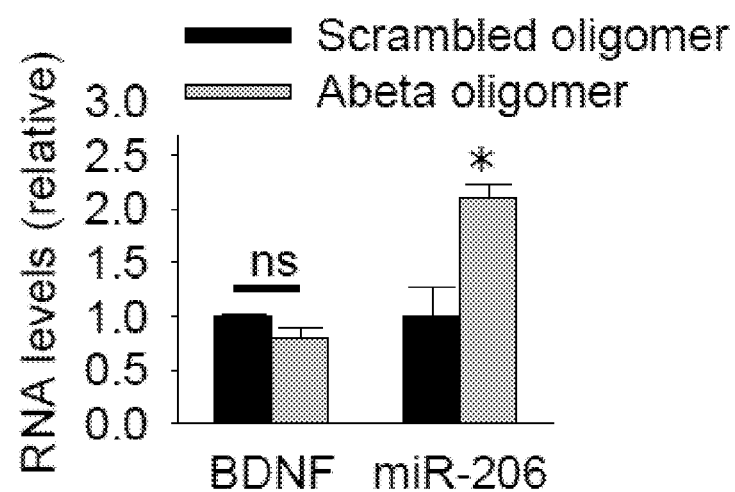
Figure 2E:
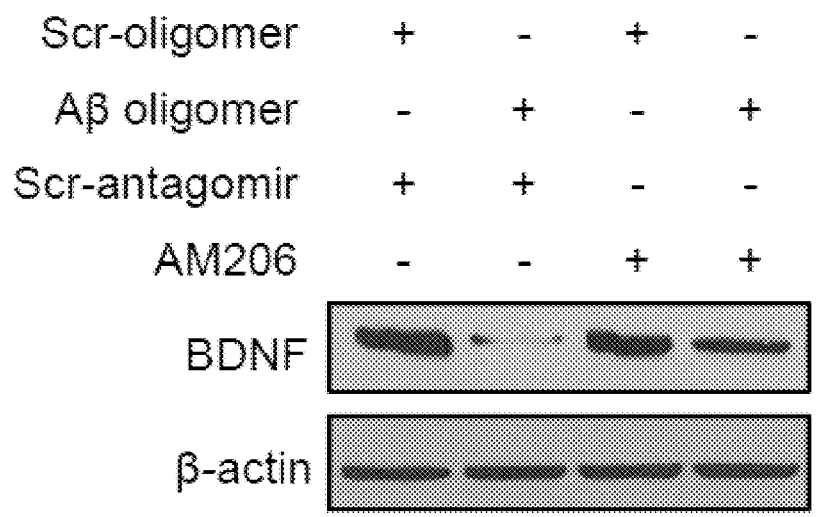
Figure 2F:
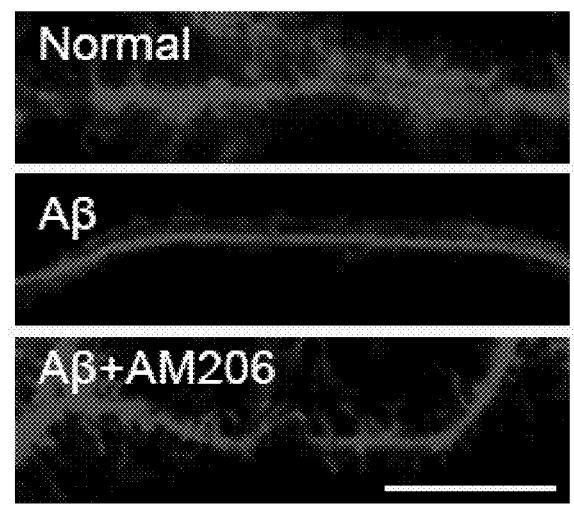
Figure 2F:
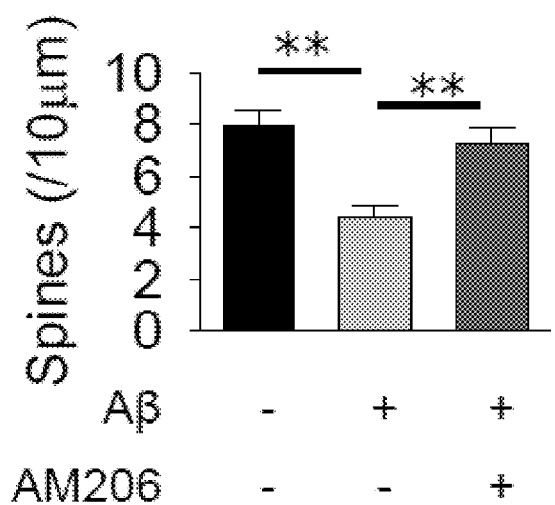

To examine this further, the present inventors transfected HeLa cells with miR-206 and luciferase vectors bearing possible target positions, including the putative binding sites of mouse BDNF mRNA (BDNF #1, #2, #3), and the total 3'-UTR of BDNF mRNA. Transfection with miR-206 reduced the luciferase activities in cells containing the vectors bearing BDNF #3 and the total 3'-UTR of BDNF mRNA, indicating that miR-206 directly suppress the translation of BDNF mRNA by binding to its 3'-UTR (FIG. 2b). The present inventors also found that transfection with miR-206 reduced the level of BDNF protein in Neuro-2a cells and HUVEC, which was neutralized by co-transfection with a miR-206 neutralizing antagomir AM206 (FIG. 2c). In Neuro-2a cells, the treatment with Aβ oligomer increased miR-206, and reduced BDNF protein levels without significantly reducing BDNF mRNA levels, suggesting translational repression of BDNF (FIG. 2d). The reduced BDNF protein level by Aβ oligomer recovered when the cells were treated with AM206 (FIG. 2e). In primary mouse hippocampal neurons, Aβ oligomer reduced the density of dendritic spines, which was recovered by AM206 treatment (FIG. 2f).

Figure 2G:
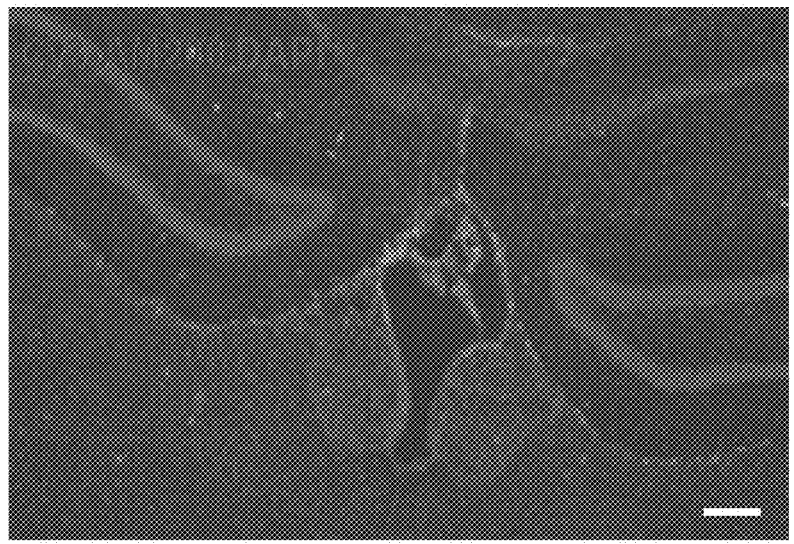
Figure 2H:
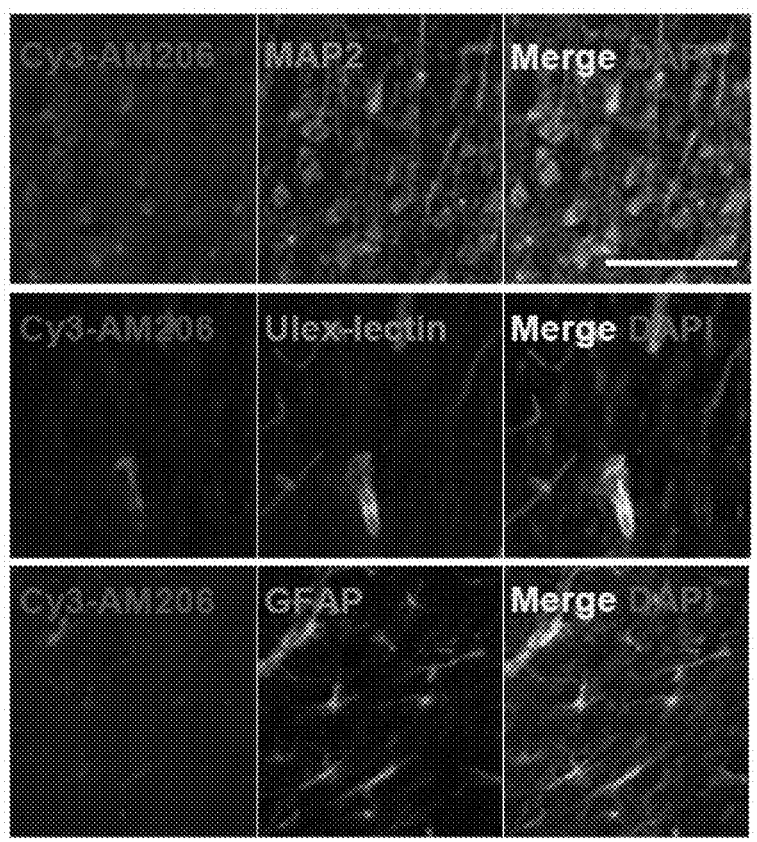
Figure 2I:
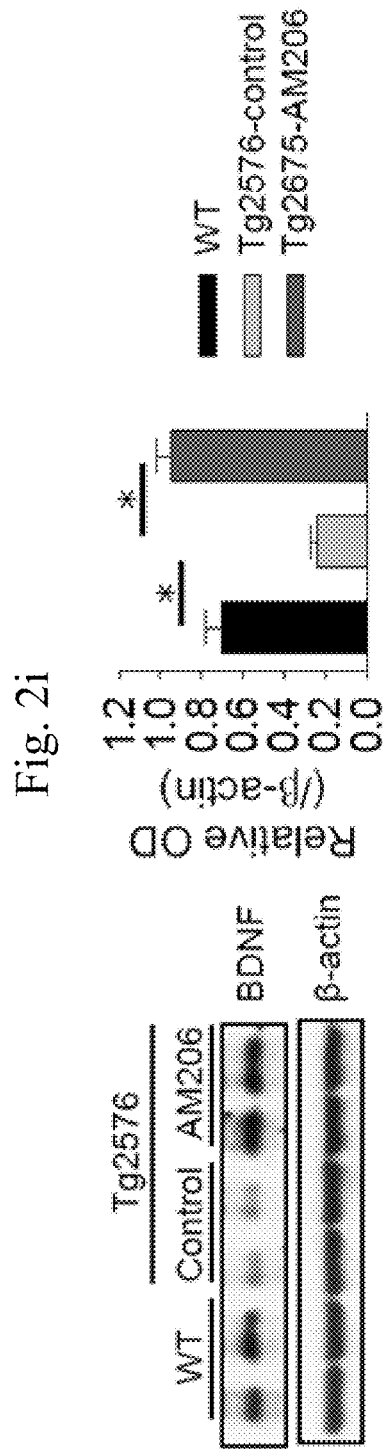

These results suggested that BDNF expression can be down-regulated by miR-206 and therefore may facilitate the progression of AD. To investigate the function of miR-206 in vivo, the present inventors injected a Cy3-labeled AM206 (Cy3-AM206) into the third ventricle of 12-month-old Tg2576 mice, and found that the Cy3-labeled AM206 (Cy3-AM206) was distributed throughout the hippocampus and surrounding tissues after one day (FIG. 2g). Cy3-AM206 was taken up by MAP2-positive neuronal cells, Ulex-lectin-positive endothelial cells, and glial fibrillary acidic protein (GFAP)-positive glial cells (FIG. 2h). Indeed, compared to a scrambled antagomir, intraventricular injection of 12-month-old Tg2576 with AM206 significantly increased the brain levels of BDNF at 1 week after the injection (FIG. 2i). In addition, injection of Tg2576 mice with AM206 activated the cAMP response element-binding and deactivated c-Jun N-terminal kinase and glycogen synthase kinase-3β, indicating that it enhances BDNF signaling.

Antagomir-206 Increased Memory Function and Synaptic Regeneration in AD Mice.

Figure 3A:
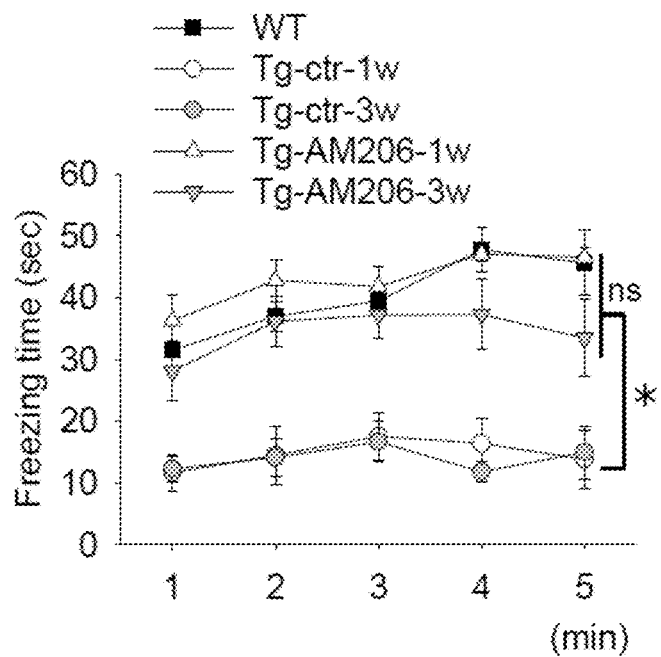
FIG. 3 represents therapeutic effects of AM206. (a) In the contextual fear conditioning test at 12 months, the freezing time was lower for control Tg2576 mice injected with scrambled miRNA 1 or 3 weeks before the tests (Tg-ctr-1 w and Tg-ctr-3 w) than for WT mice. AM206 treatment in Tg2576 mice either 1 week (Tg-AM206-1 w) or 3 weeks (Tg-AM206-3 w) before the test increased the freezing time (n=5 per group, Kruskall-Wallis analysis followed by Mann-Whitney U test), suggesting increased hippocampal memory function. (b) In the cued conditioning test, there was no difference between the groups (n=5 per group). The dotted line indicates the sound cue. (c) In Y-maze test, the Tg-AM206-1 w mice showed better alternation behaviors than the Tg-ctr-1 w mice. The Tg-AM206-3 w mice showed similar alternation behaviors as the Tg-ctr-3 w mice (n=5 per group). (d) Synaptophysin expression was higher in Tg-AM206-1 w and Tg-AM206-3 w mice than in the corresponding control Tg2576 mice, suggesting that AM206 increased synaptic density (n=6 per group). Scale bar, 200 μm. (e) The number of doublecortin (Dcx)-positive cells (arrows) in the subgranular layer of the dentate gyms was also higher in Tg-AM206-1 w and Tg-AM206-3 w mice than in control Tg2576 mice, suggesting that AM206 enhanced neurogenesis (n=6 per group). Scale bar, 50 μm. *P<0.05. **P<0.01. ns, not significant. Bars indicate means±s.e.m.
Figure 3B:
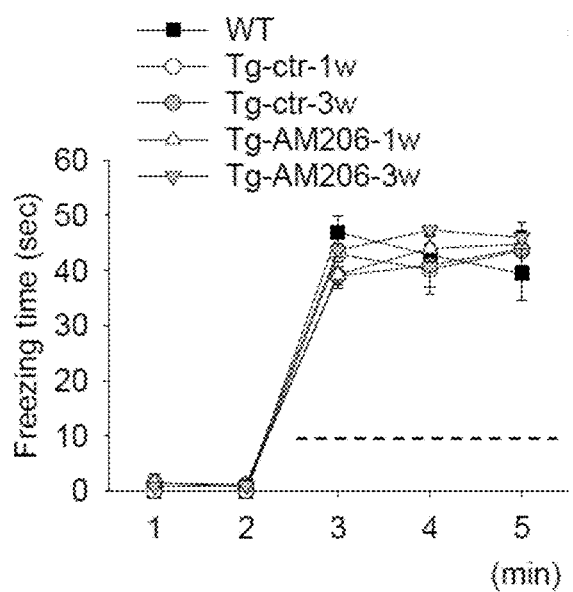

The present inventors next sought to determine the therapeutic effect of enhancing BDNF by injecting AM206 into the third ventricle of Tg2576 mice either 1 week or 3 weeks before memory tests at 12 months. In the contextual fear conditioning test, the freezing time for Tg2576 control mice was lower than for WT mice, suggesting impaired hippocampal memory in the Tg2576 mice (FIG. 3a). Both 1 and 3 weeks after injection, the freezing time was higher for Tg2576 mice treated with AM206 than for control Tg2576 mice, indicating that AM206 increased hippocampal memory function for at least 3 weeks. In the cued conditioning test, in which amygdala plays the major role, there was no difference between the groups (FIG. 3b). In a Y-maze test, the Tg2576 mice treated with AM206 had better alternation behaviors than the Tg2576 control mice when measured 1 week after injection (FIG. 3c). However, AM206 did not affect the total plaque area in the cortex or hippocampus as measured by Thioflavin-S staining, nor did it affect the brain level of Aβ40 or Aβ42 as measured by ELISA. Therefore, the improvement of memory by AM206 mice was due to mechanisms other than changes in Aβ levels.

Figure 3D:
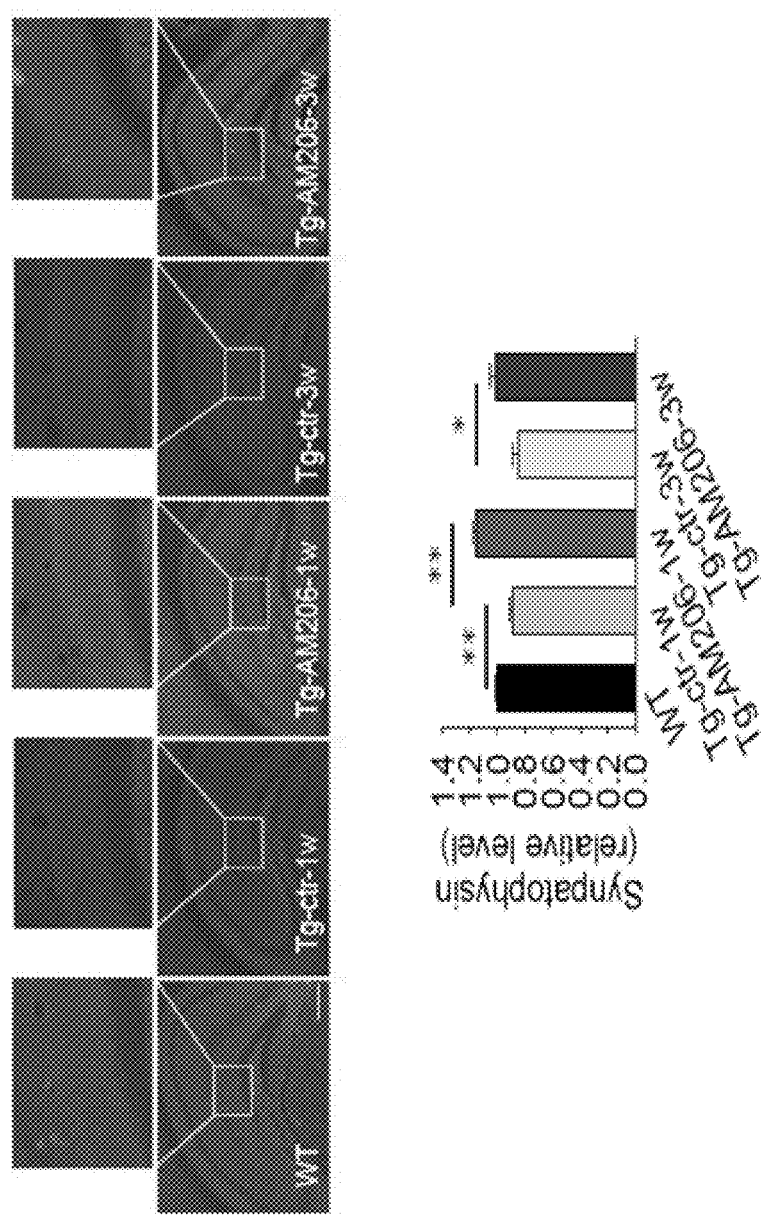
Figure 3E:
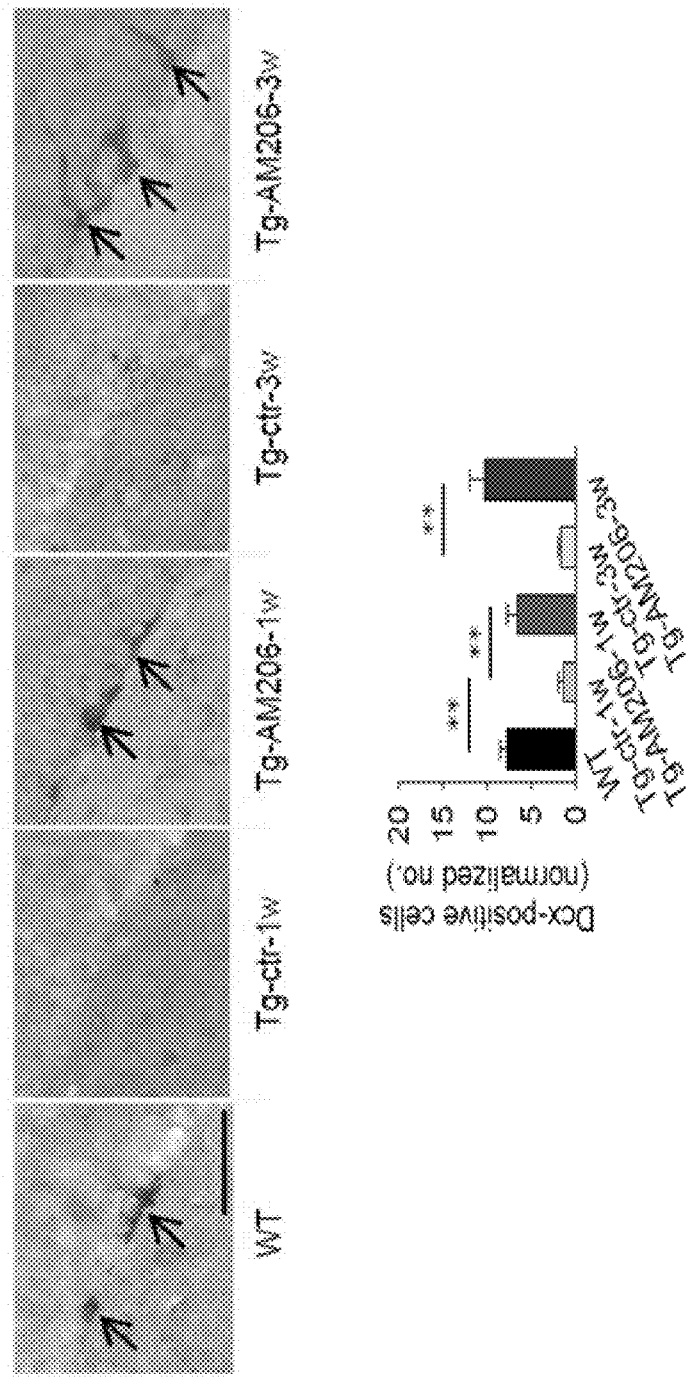

Because AM206 increased BDNF expression, the present inventors measured its effects on the hippocampal synaptophysin levels and the number of doublecortin-positive cells. Tg2576 control mice had lower synaptophysin levels than WT mice (FIG. 3d). Injection of Tg2576 mice with AM206 either 1 or 3 weeks before the test increased synaptophysin expression compared to Tg2576 control mice (FIG. 3d), suggesting increased synaptic density. In addition, although Tg2576 control mice had fewer doublecortin-positive cells in the hippocampal dentate gyrus than WT mice, mice injected with AM206 1 or 3 weeks before staining had more doublecortin-positive cells than Tg2576 control mice (FIG. 3e), indicating enhanced hippocampal neurogenesis.

Intranasal Administration Effect on Antagomir-206

Figure 4B:
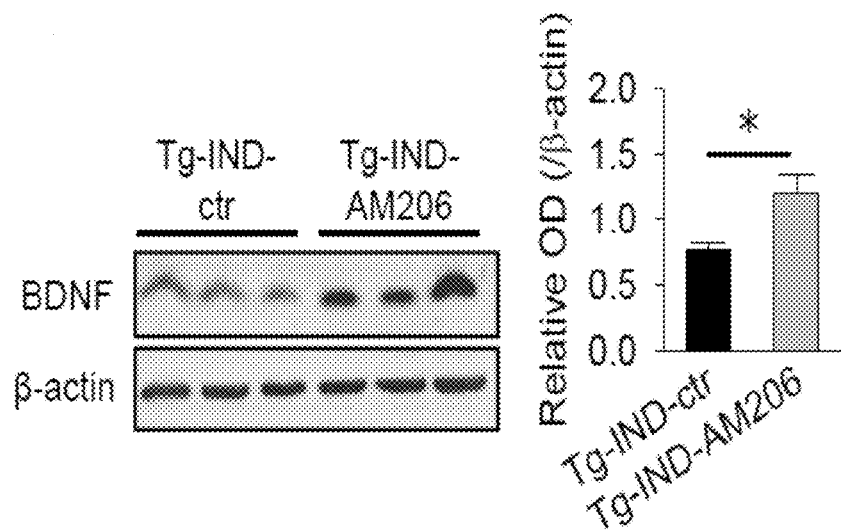
FIG. 4 represents intranasal delivery of the antagomir. (a) Following intranasal delivery, Cy3-labeled AM206 was distributed throughout olfactory bulb, cortex, and hippocampus after 24 h. Vehicle-administered control brain expressed no Cy3 fluorescence. Scale bar, 50 μm. (b) Intranasal delivery of AM206 in Tg2576 mice (Tg-IND-AM206) increased the whole brain level of BDNF compared to control Tg2576 mice treated with vehicle (Tg-IND-ctr) at 1 week, as shown by Western blotting (left) and densitometry (right). (c) In a contextual fear conditioning test performed 1 week after treatment (n=5 per group), the freezing time was higher for Tg-IND-AM206 than for Tg-IND-ctr. (d) In the cued conditioning test, there was no difference between the groups (n=5 per group). The dotted line indicates the sound cue. (e) The Y maze test revealed that intranasal delivery of AM206 increased the alternation behavior compared to control mice (n=5 per group). * P<0.05. Bars show means±s.e.m.
Figure 4C:
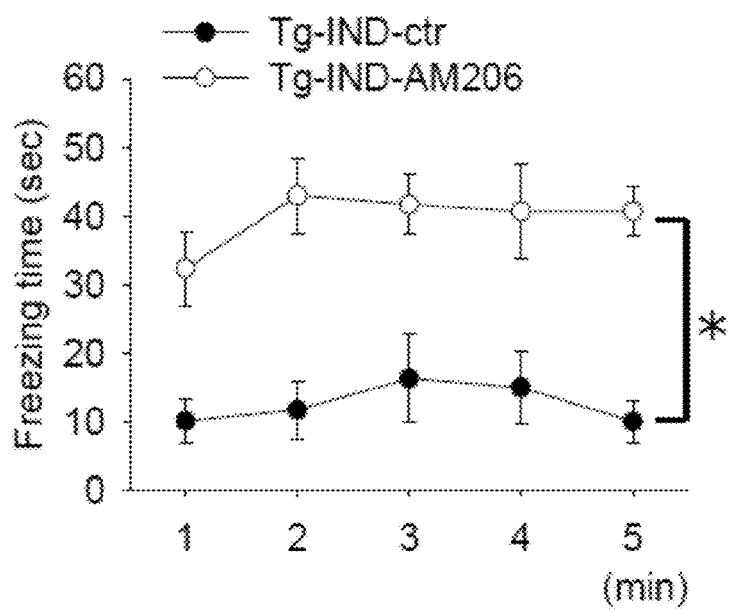
Figure 4D:
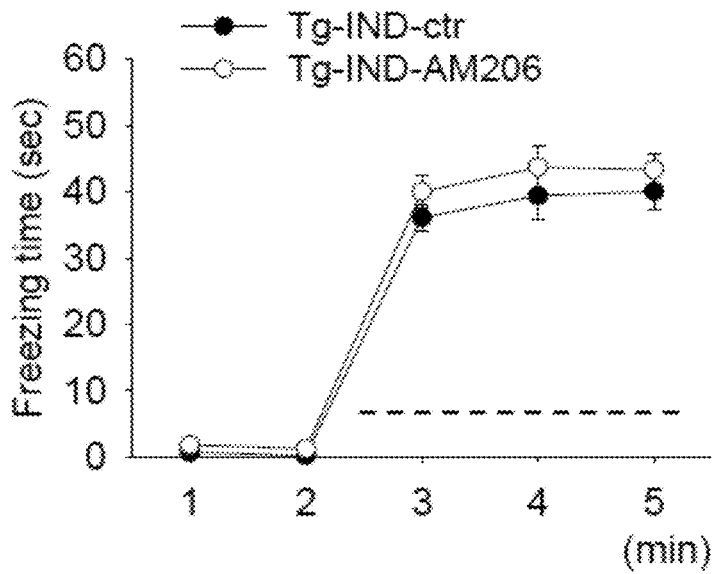
Figure 4E:
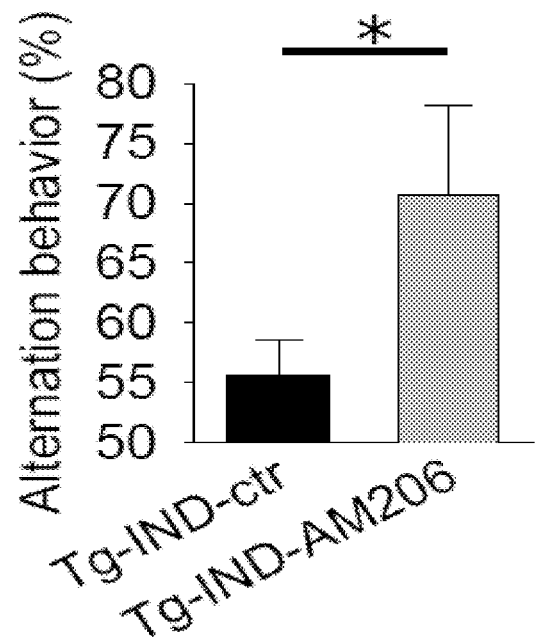

Therapeutics can rapidly gain access to the brain following intranasal administration along olfactory nerve pathway from the nasal cavity directly to the brain, bypassing blood-brain barrier. This noninvasive and convenient method of drug delivery has been effective even in AD patients. The present inventors investigated whether the antagomir can be delivered via this route as well. Indeed, intranasally delivered Cy3-labeled AM206 was detected in olfactory bulb, cortex, and hippocampus of Tg2576 mice after 24 hrs (FIG. 4a). A number of MAP2-positive neuronal cells and Ulex-lectin-positive endothelial cells, and few GFAP-positive glial cells, were labeled with Cy3-AM206. Intranasally administered AM206 increased the brain level of BDNF compared to the vehicle administration in the Tg2576 mice after 1 week (FIG. 4b). In addition, intranasal delivery of AM206 increased the memory function of Tg2576 mice as measured by fear conditioning tests (FIG. 4c,d) and Y-maze tests after 1 week (FIG. 4e). These results showed that intranasal delivery of the antagomir to the brain is a feasible method.

DISCUSSION

Previous studies on the changes in and roles of miRNAs in AD have identified several miRNAs in the brain that regulate BACE1/β-secretase expression or NF-κB-induced inflammation, including miR-29a/b-1, miR-107, miR-146a, miR-298, and miR-328. miR-206 is normally expressed in muscle tissue, and participates in myogenesis and the regeneration of neuromuscular junctions. The level of miR-206 is very low in normal brains but is expressed at aberrantly high level in AD. Experimentally, the upregulations of miR-206 in brain have been observed after cerebral ischemia and neurotoxicant exposure. In human, miR-206 expression is elevated in the frontal cortex of amyotrophic lateral sclerosis patients, and genetic variations of miR-206 have been found in schizophrenia patients. Our current data indicate that miR-206 also participates in the pathogenesis of AD by suppressing BDNF levels. Therefore, the present invention provides a rationale for translational approaches using miR-206 modulators for the treatment of AD.

Intracerebral deliveries of BDNF via lentiviral vectors, by protein infusion pump, or using neural stem cells improve memory function and synaptic density in AD models. However, delivering neurotrophic factors to the brain suffers from invasiveness, device-related adverse events, and the emergence of neutralizing antibodies. The present invention suspects that intranasal delivery of AM206 could be a feasible alternative method, and that similar approaches using antagomirs would be possible in other brain disorders as well.

REFERENCES

Boissonneault V, Plante I, Rivest S, Provost P. MicroRNA-298 and microRNA-328 regulate expression of mouse beta-amyloid precursor protein-converting enzyme 1. J Biol Chem. 2009; 284:1971-81.

Bonauer A, Carmona G, Iwasaki M, Mione M, Koyanagi M, Fischer A, Burchfield J, Fox H, Doebele C, Ohtani K, Chavakis E, Potente M, Tjwa M, Urbich C, Zeiher A M, Dimmeler S. MicroRNA-92a controls angiogenesis and functional recovery of ischemic tissues in mice. Science. 2009; 324:1710-3.

Braak H, Braak E. Evolution of the neuropathology of Alzheimer's disease. Acta Neurol Scand Suppl. 1996; 165:3-12.

Bramham C R, Messaoudi E. BDNF function in adult synaptic plasticity: the synaptic consolidation hypothesis. Prog Neurobiol. 2005; 76:99-125.

Carro E, Trejo J L, Gomez-Isla T, LeRoith D, Torres-Aleman I. Serum insulin-like growth factor I regulates brain amyloid-beta levels. Nat Med. 20028:1390-7.

Carro E, Trejo J L, Spuch C, Bohl D, Heard J M, Torres-Aleman I. Blockade of the insulin-like growth factor I receptor in the choroid plexus originates Alzheimer's-like neuropathology in rodents: new cues into the human disease? Neurobiol Aging. 2006; 27:1618-31.

Chabriat H, Joutel A, Dichgans M, Tournier-Lasserve E, Bousser MG. Cadasil. Lancet Neurol. 2009; 8:643-53.

Cogswell J P, Ward J, Taylor I A, Waters M, Shi Y, Cannon B, Kelnar K, Kemppainen J, Brown D, Chen C, Prinjha R K, Richardson J C, Saunders A M, Roses A D, Richards C A. Identification of miRNA changes in Alzheimer's disease brain and CSF yields putative biomarkers and insights into disease pathways. J Alzheimers Dis. 2008;14:27-41.

Cuellar T L, Davis T H, Nelson P T, Loeb G B, Harfe B D, Ullian E, McManus M T. Dicer loss in striatal neurons produces behavioral and neuroanatomical phenotypes in the absence of neurodegeneration. Proc Natl Acad Sci USA. 2008 105:5614-9.

Das I, Craig C, Funahashi Y, Jung K M, Kim T W, Byers R, Weng A P, Kutok J L, Aster J C, Kitajewski J. Notch oncoproteins depend on gamma-secretase/presenilin activity for processing and function. J Biol Chem. 2004; 279:30771-30780.

Elmén J, Lindow M, Schütz S, Lawrence M, Petri A, Obad S, Lindholm M, Hedtjärn M, Hansen H F, Berger U, Gullans S, Kearney P, Sarnow P, Straarup E M, Kauppinen S. LNA-mediated microRNA silencing in non-human primates. Nature. 2008 452:896-9.

Ernfors P, Bramham CR. The coupling of a trkB tyrosine residue to LTP. Trends Neurosci. 2003; 26:171-3.

Hansen T, Olsen L, Lindow M, Jakobsen K D, Ullum H, Jonsson E, ndreassen O A, Djurovic S, Melle I, Agartz I, Hall H, Timm S, Wang A G, Werge T. Brain expressed microRNAs implicated in schizophrenia etiology. PLoS One. 2007; 2:e873.

Hébert S S, Horré K, Nicolaï L, Papadopoulou A S, Mandemakers W, Silahtaroglu A N, Kauppinen S, Delacourte A, De Strooper B. Loss of microRNA cluster miR-29a/b-1 in sporadic Alzheimer's disease correlates with increased BACE1/beta-secretase expression. Proc Natl Acad Sci USA. 2008 105:6415-20.

Hebert S S, De Strooper B. Alterations of the microRNA network cause neurodegenerative disease. Trends Neurosci. 2009; 32:199-206.

Hsiao K, Chapman P, Nilsen S, Eckman C, Harigaya Y, Younkin S, Yang F, Cole G. Correlative memory deficits, Abeta elevation, and amyloid plaques in transgenic mice. Science. 1996; 274:99-102.

Jacobsen J S, Wu C C, Redwine J M, Comery T A, Arias R, Bowlby M, Martone R, Morrison J H, Pangalos M N, Reinhart P H, Bloom F E. Early-onset behavioral and synaptic deficits in a mouse model of Alzheimer's disease. Proc Natl Acad Sci US 2006; 103:5161-6.

Jeon D, Song I, Guido W, Kim K, Kim E, Oh U, Shin H S. Ablation of Ca2+ channel beta3 subunit leads to enhanced N-methyl-D-aspartate receptor-dependent long term potentiation and improved long term memory. J Biol Chem. 2008 283:12093-101.

Karres J S, Hilgers V, Carrera I, Treisman J, Cohen S M. The conserved microRNA miR-8 tunes atrophin levels to prevent neurodegeneration in Drosophila. Cell. 2007; 131: 136-45.

Kim J, Inoue K, Ishii J, Vanti W B, Voronov S V, Murchison E, Hannon G, Abeliovich A. A MicroRNA feedback circuit in midbrain dopamine neurons. Science. 2007 317:1220-4.

Kim V N, Han J, Siomi M C. Biogenesis of small RNAs in animals. Nat Rev Mol Cell Biol. 2009; 10:126-39.

Lanford R E, Hildebrandt-Eriksen E S, Petri A, Persson R, Lindow M, Munk M E, Kauppinen S, Ørum H. Therapeutic silencing of microRNA-122 in primates with chronic hepatitis C virus infection. Science. 2010; 327:198-201.

Lang A E, Gill S, Patel N K, Lozano A, Nutt J G, Penn R, Brooks D J, Hotton G, Moro E, Heywood P, Brodsky M A, Burchiel K, Kelly P, Dalvi A, Scott B, Stacy M, Turner D, Wooten V G, Elias W J, Laws E R, Dhawan V, Stoessl A J, Matcham J, Coffey R J, Traub M. Randomized controlled trial of intraputamenal glial cell line-derived neurotrophic factor infusion in Parkinson disease. Ann Neurol. 2006 59:459-466.

Lee S T, Chu K, Jung K H, Im W S, Park J E, Lim H C, Won C H, Shin S H, Lee S K, Kim M, Roh J K. Slowed progression in models of Huntington disease by adipose stem cell transplantation. Ann Neurol. 2009 66:671-81.

Lukiw W J, Zhao Y, Cui J G. An NF-kappaB-sensitive micro RNA-146a-mediated inflammatory circuit in Alzheimer disease and in stressed human brain cells. J Biol Chem. 2008; 283:31315-22.

Maes O C, Chertkow H M, Wang E, Schipper H M. MicroRNA: Implications for Alzheimer Disease and other Human CNS Disorders. Curr Genomics. 2009 10:154-68.

Nagahara A H, Merrill D A, Coppola G, Tsukada S, Schroeder B E, Shaked G M, Wang L, Blesch A, Kim A, Conner J M, Rockenstein E, Chao M V, Koo E H, Geschwind D, Masliah E, Chiba A A, Tuszynski M H. Neuroprotective effects of brain-derived neurotrophic factor in rodent and primate models of Alzheimer's disease. Nat Med. 2009; 15:331-7.

Packer A N, Xing Y, Harper S Q, Jones L, Davidson B L. The bifunctional microRNA miR-9/miR-9* regulates REST and CoREST and is downregulated in Huntington's disease. J Neurosci. 2008; 28:14341-6.

Phillips H S, Hains J M, Armanini M, Laramee G R, Johnson S A, Winslow J W. BDNF mRNA is decreased in the hippocampus of individuals with Alzheimer's disease. Neuron. 1991; 7:695-702.

Querfurth H W, LaFerla F M. Alzheimer's disease. N Engl J Med 2010; 362:329-44.

Rao P K, Kumar R M, Farkhondeh M, Baskerville S, Lodish H F. Myogenic factors that regulate expression of muscle-specific microRNAs. Proc Natl Acad Sci USA. 2006; 103:8721-6.

Sarter M, Bodewitz G, Stephens D N. Attenuation of scopolamine-induced impairment of spontaneous alteration behaviour by antagonist but not inverse agonist and agonist beta-carbolines. Psychopharmacology. 1988; 94:491-495.

Schaefer A, O'Carroll D, Tan C L, Hillman D, Sugimori M, Llinas R, Greengard P. Cerebellar neurodegeneration in the absence of microRNAs. J Exp Med. 2007 204:1553-8.

Sethi P, Lukiw W J. Micro-RNA abundance and stability in human brain: specific alterations in Alzheimer's disease temporal lobe neocortex. Neurosci Lett. 2009; 459:100-4.

Selkoe D J. Alzheimer's disease is a synaptic failure. Science. 2002; 298:789-91.

Shaked I, Meerson A, Wolf Y, Avni R, Greenberg D, Gilboa-Geffen A, Soreq H. MicroRNA-132 potentiates cholinergic anti-inflammatory signaling by targeting acetylcholinesterase. Immunity. 2009; 31:965-73.

Shioya M, Obayashi S, Tabunoki H, Arima K, Saitoh Y, Ishida T, Satoh J. Aberrant microRNA expression in the brains of neurodegenerative diseases: miR-29a decreased in Alzheimer disease brains targets neuron navigator-3. Neuropathol Appl Neurobiol. 2010. 10.1111/j.1365-2990.2010.01076.x Wang W X, Rajeev B W, Stromberg A J, Ren N, Tang G, Huang Q, Rigoutsos I, Nelson P T. The expression of microRNA miR-107 decreases early in Alzheimer's disease and may accelerate disease progression through regulation of beta-site amyloid precursor protein-cleaving enzyme 1. J Neurosci. 2008; 28:1213-23.

Wang X, Liu P, Zhu H, Xu Y, Ma C, Dai X, Huang L, Liu Y, Zhang L, Qin C. miR-34a, a microRNA up-regulated in a double transgenic mouse model of Alzheimer's disease, inhibits bcl2 translation. Brain Res Bull. 2009; 80:268-73.

Williams A H, Valdez G, Moresi V, Qi X, McAnally J, Elliott J L, Bassel-Duby R, Sanes J R, Olson E N. MicroRNA-206 delays ALS progression and promotes regeneration of neuromuscular synapses in mice. Science. 2009; 326:1549-54.

Wu Z, Guo H, Chow N, Sallstrom J, Bell R D, Deane R, Brooks A I, Kanagala S, Rubio A, Sagare A, Liu D, Li F, Armstrong D, Gasiewicz T, Zidovetzki R, Song X, Hofman F, Zlokovic B V. Role of the MEOX2 homeobox gene in neurovascular dysfunction in Alzheimer disease. Nat Med. 2005; 11:959-65.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating an Alzheimer's disease, comprising administering to a subject in need thereof a pharmaceutical composition comprising:
   (a) a pharmaceutically effective amount of an antisense oligonucleotide having perfect complementarity to SEQ ID NO:1; and
   (b) a pharmaceutically acceptable carrier, wherein the antisense oligonucleotide is a 2'—O—$C_{1-3}$ alkyl ribonucleotide.

2. The method according to claim 1, wherein administration is an intranasal administration.

* * * * *

SEQUENCE LISTING

<160> NUMBER OF SEQ ID NOS: 5

<210> SEQ ID NO 1
<211> LENGTH: 22
<212> TYPE: RNA
<213> ORGANISM: Homo sapiens

<400> SEQUENCE: 1
uggaauguaa ggaagugugu gg                                          22

<210> SEQ ID NO 2
<211> LENGTH: 29
<212> TYPE: RNA
<213> ORGANISM: Artificial Sequence
<220> FEATURE:
<223> OTHER INFORMATION: Partial BDNF 3'-UTR (BDNF #1)

<400> SEQUENCE: 2
acaacuuuaa aagucugcau uacauuccu                                   29

<210> SEQ ID NO 3

```
<211> LENGTH: 27
<212> TYPE: RNA
<213> ORGANISM: Artificial Sequence
<220> FEATURE:
<223> OTHER INFORMATION: Partial BDNF 3'-UTR (BDNF #2)

<400> SEQUENCE: 3
aacaaaaauu ggaaccaaaa cauuccg                                              27

<210> SEQ ID NO 4
<211> LENGTH: 23
<212> TYPE: RNA
<213> ORGANISM: Artificial Sequence
<220> FEATURE:
<223> OTHER INFORMATION: Partial BDNF 3'-UTR (BDNF #3)

<400> SEQUENCE: 4
ggaaugguac uugagacauu ccu                                                  23

<210> SEQ ID NO 5
<211> LENGTH: 21
<212> TYPE: RNA
<213> ORGANISM: Mus musculus

<400> SEQUENCE: 5
ggugugugaa gaauguaagg u                                                    21
```